(12) United States Patent
Ritter et al.

(10) Patent No.: US 8,071,812 B1
(45) Date of Patent: Dec. 6, 2011

(54) PROCESS FOR THE SYNTHESIS OF 1,3-DIAMINO-4,6-DINITROBENZENE

(75) Inventors: Joachim C. Ritter, Wilmington, DE (US); Annalisa Hargis, Wilmington, DE (US)

(73) Assignee: E.I du Pont de Nemours & Company, Wilmington, DE (US)

( * ) Notice: Subject to any disclaimer, the term of this patent is extended or adjusted under 35 U.S.C. 154(b) by 334 days.

(21) Appl. No.: 12/335,997

(22) Filed: Dec. 16, 2008

Related U.S. Application Data

(60) Provisional application No. 61/014,557, filed on Dec. 18, 2007.

(51) Int. Cl.
*C07C 209/00* (2006.01)

(52) U.S. Cl. ........ 564/416; 564/305; 564/306; 564/441; 564/415

(58) Field of Classification Search .................. None
See application file for complete search history.

(56) References Cited

U.S. PATENT DOCUMENTS 3,783,137 A    1/1974   Gerber

FOREIGN PATENT DOCUMENTS

JP           2003-292476      * 10/2003

OTHER PUBLICATIONS

Boyer et al, Journal of the American Chemical Society, 1960, 82, 2213-15.*
Knoblock et al, Chemische Berichte, 1958, 91, 2562-6.*
Blanksma, Chemisch Weekblad, 1913, 9, 968-73.*
Boyer et al., The Preparation of 6,7-Disubstituted Quinoxalines, J. Am. Chem. Soc., 1960, vol. 82:2213-2215.
Knobloch et al., Synthese Von 2.6-Disubstituierten Benzo[1.2.4.5]Bisimidazolen, Chem. Ber., 1958, vol. 91:2562-2566.
U.S. Appl. No. 12/335,997, filed Dec. 16, 2008, Applicant Joachim C. Ritter.
R. Nietzki et al., Synthese Von Symmetrischem Tetramidobenzol Mittels Dinitrodichlorbenzol, 1897, vol. 30:1666-1669.

* cited by examiner

*Primary Examiner* — Sudhakar Katakam

(57) ABSTRACT

A process is provided for the preparation of 1,3-diamino-4,6-dinitrobenzene by amination of 1,3-dihalo-4,6-dinitrobenzene. The presence of water advantageously results in a highly pure product, free or essentially free of glycol ether impurities.

15 Claims, No Drawings

PROCESS FOR THE SYNTHESIS OF 1,3-DIAMINO-4,6-DINITROBENZENE

This application claims priority under 35 U.S.C. §119(e) from, and claims the benefit of, U.S. Provisional Application No. 61/014,557, filed Dec. 18, 2007, which is by this reference incorporated in its entirety as a part hereof for all purposes.

TECHNICAL FIELD

This disclosure relates to a method of making 1,3-diamino-4,6-dinitrobenzene.

BACKGROUND

The compound 1,3-diamino-4,6-dinitrobenzene ("DADNB"), which is represented by the structure of the following Formula (I):

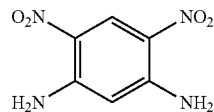

is conventionally used as a starting material or intermediate in the preparation of a variety of products, which include dyes, pharmaceuticals, and monomers for incorporation into polybenzimidazole polymers such as those described in U.S. Pat. No. 3,783,137.

DADNB can be made by contacting a suspension of 1,3-dichloro-4,6-dinitrobenzene ("DCDNB") in glycol with ammonia and heating, according, for example, to the method described in Boyer et al, *J. Am. Chem. Soc.*, 82, 2213 (1960). Current processes for making DADNB produce a by-product glycol ether, as represented by the structure of the following Formula (II):

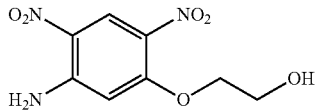

DADNB is very difficult and costly to recrystallize because of its poor solubility in common solvents, and this glycol ether impurity thus remains in the final DADNB product. As a consequence, the purity and properties of downstream products made directly or remotely from DADNB, such as 1,2,4,5-tetraminobenzene ("TAB"), is compromised.

For example, TAB is a precursor to high-performance polymers such as polybenzimidazoles, which are used to make high-performance, high-strength fibers. The purity of the precursors affects the polymer molecular weight that can be achieved, which in turn determines whether satisfactory fibers can be produced.

There thus remains a need for an improved process for making high-purity 1,3-diamino-4,6-dinitrobenzene.

SUMMARY

The inventions disclosed herein include processes for the preparation of a 1,3-diamino-4,6-dinitrobenzene, processes for the preparation of products into which a 1,3-diamino-4,6-dinitrobenzene can be converted, the use of such processes, and the products obtained and obtainable by such processes.

Features of certain of the processes of this invention are described herein in the context of one or more specific embodiments that combine various such features together. The scope of the invention is not, however, limited by the description of only certain features within any specific embodiment, and the invention also includes (1) a subcombination of fewer than all of the features of any described embodiment, which subcombination may be characterized by the absence of the features omitted to form the subcombination; (2) each of the features, individually, included within the combination of any described embodiment; and (3) other combinations of features formed by grouping only selected features taken from two or more described embodiments, optionally together with other features as disclosed elsewhere herein. Some of the specific embodiments of the processes hereof are as follows:

One embodiment of this invention provides a process for preparing 1,3-diamino-4,6-dinitrobenzene, which is represented by the structure of the following Formula (I):

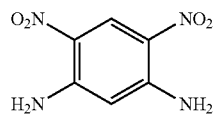

by (a) providing a reaction mixture that comprises 1,3-dihalo-4,6-dinitrobenzene, which is represented by the structure of the following Formula (III):

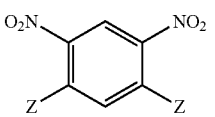

wherein each Z is independently Cl or Br, in a solvent in the presence of ammonia and about 2 to about 25 wt % water (based on the combined weight of water and solvent in the reaction mixture); and (b) heating the reaction mixture to convert the 1,3-dihalo-4,6-dinitrobenzene to 1,3-diamino-4,6-dinitrobenzene.

An advantageous effect of a process hereof is that the presence of even a small amount of water during the amination process results in a higher purity DADNB product.

DETAILED DESCRIPTION

In one embodiment of a process hereof, a process is provided for preparing 1,3-diamino-4,6-dinitrobenzene, which is represented by the structure of the following Formula (I):

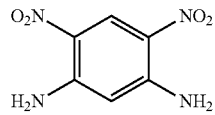

by (a) providing a reaction mixture that comprises 1,3-dihalo-4,6-dinitrobenzene, which is represented by the structure of the following Formula (III):

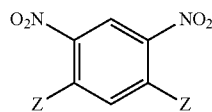

wherein each Z is independently Cl or Br, in a solvent in the presence of ammonia and about 2 to about 25 wt % water (based on the combined weight of water and solvent in the reaction mixture); and (b) heating the reaction mixture to convert the 1,3-dihalo-4,6-dinitrobenzene to 1,3-diamino-4,6-dinitrobenzene.

In a preferred embodiment, one or both of the Zs in the structure of Formula (III) is Cl.

In another embodiment of a process hereof, the process involves (c) forming a suspension of 1,3-dihalo-4,6-dinitrobenzene in a mixture of solvent and water, wherein the suspension comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); and (d) (i) heating the suspension, and (ii) contacting the suspension with gaseous $NH_3$, to convert the 1,3-dihalo-4,6-dinitrobenzene to 1,3-diamino-4,6-dinitrobenzene.

More specifically in the above embodiment, the suspension is heated to a temperature in the range of about 100° C. to about 160° C., preferably about 130° C. to about 150° C., and more preferably about 140° C., to dissolve the 1,3-dihalo-4,6-dinitrobenzene in the solvent. Heating is for a time sufficient to convert the 1,3-dihalo-4,6-dinitrobenzene to 1,3-diamino-4,6-dinitrobenzene. The resulting solution is contacted at the selected temperature with gaseous $NH_3$ for approximately four to eight hours close to ambient pressure, and the gaseous $NH_3$ is fed as it is consumed.

In a further embodiment of a process hereof, the process involves (e) (i) forming a suspension of 1,3-dihalo-4,6-dinitrobenzene in solvent, (ii) heating the suspension, and (iii) contacting the heated suspension with an aqueous ammonia solution to form a reaction mixture that comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture); and (f) heating the reaction mixture to convert the 1,3-dihalo-4,6-dinitrobenzene to 1,3-diamino-4,6-dinitrobenzene.

More specifically in the above embodiment, the suspension and/or reaction mixture is heated to a temperature in the range of about 100° C. to about 160° C., preferably about 130° C. to about 150° C., and more preferably about 140° C., to dissolve the 1,3-dihalo-4,6-dinitrobenzene in the solvent. Heating is for a time sufficient to convert the 1,3-dihalo-4,6-dinitrobenzene to 1,3-diamino-4,6-dinitrobenzene. The resulting solution is contacted at that temperature with aqueous ammonia (typical concentration, about 28 wt % $NH_3$) for approximately four to eight hours close to ambient pressure; the aqueous ammonia is fed as it is consumed. The aqueous ammonia solution is added such that the amount of $NH_3$ released through the gas outlet is kept at minimum, and stirring is kept constant throughout the reaction. During addition of the aqueous ammonia solution, the amount of water in the reaction mixture increases from about 2% to about 25 wt % based on water plus solvent. In this embodiment, the amount of water, initially about 2 wt % based on water plus solvent, increases steadily up to about 17% at reaction completion. Since the glycol ether byproduct forms only at high conversions, the amount of water added is sufficient. An advantage to this embodiment is that one can use an aqueous solution of ammonia (also referred to as ammonium hydroxide or "$NH_4OH$") which is easier to handle and less hazardous than gaseous ammonia. Reaction rates are also higher when an aqueous solution of ammonia is used.

In yet another embodiment of the process hereof, rather than forming a suspension of DHDNB in solvent and water and then feeding gaseous ammonia, or rather than forming a suspension of DHDNB in solvent and then feeding an aqueous solution of ammonia, the DHDNB is instead contacted with a feed stream containing solvent, water and $NH_3$, thereby forming the reaction mixture. This allows for easy adjustment of the relative proportions of solvent, water and $NH_3$ at any time during the amination process.

This embodiment of the process thus involves (g) contacting 1,3-dihalo-4,6-dinitrobenzene with a feed that comprises solvent, water and $NH_3$ to form a reaction mixture that comprises a suspension of about 10 to about 25 wt % 1,3-dihalo-4,6-dinitrobenzene (based on the total weight of the whole reaction mixture) and about 2 to about 25 wt % water (based on the combined weight of water and solvent in the reaction mixture); and (h) heating the reaction mixture to convert the 1,3-dihalo-4,6-dinitrobenzene to 1,3-diamino-4,6-dinitrobenzene.

More specifically in the above embodiment, the reaction mixture is heated to a temperature in the range of about 100° C. to about 160° C., preferably about 130° C. to about 150° C., and more preferably about 140° C., to dissolve the 1,3-dihalo-4,6-dinitrobenzene. Heating is for a time sufficient to convert the 1,3-dihalo-4,6-dinitrobenzene to 1,3-diamino-4,6-dinitrobenzene. The reaction mixture is heated for approximately four to eight hours, close to ambient pressure.

In any of the above embodiments, at reaction completion, the 1,3-diamino-4,6-dinitrobenzene thereby produced may be filtered, typically at about 60° C., and washed with a solvent such as glycol and then water. The mother liquor (filtrate) containing the solvent can be collected and the solvent distilled and recycled; when this is done, purges are drawn to prevent accumulation. A wet cake of 1,3-diamino-4,6-dinitrobenzene can be dried if it is the final product. Alternatively, it can be slurried with water as a suspension and transferred to another reactor for further processing.

In any of the embodiments hereof, a solvent suitable for use includes an organic solvent inert to the reaction such as an aliphatic dihydric alcohol such as ethylene glycol ("glycol").

DHDNB suitable for use herein may be prepared, for example, by nitration of 1,3-dihalobenzene as described in Knobloch et. al, Chem. Ber. 91, 2563 (1958); or according to the method described in U.S. Provisional Application No. 61/014,515, which is by this reference incorporated in its entirety as a part hereof for all purposes. Typically, the DHDNB used is 1,3-dichloro-4,6-dinitrobenzene ("DHDNB"); that is, Z=Cl.

U.S. Provisional Application No. 61/014,515 provides a process for preparing a 1,3-dihalo-4,6-dinitrobenzene by (a) admixing a 1,3-dihalobenzene, which is represented by the structure of the following Formula (IX):

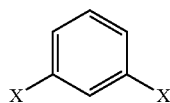

wherein each X is independently Cl or Br, with fuming nitric acid, sulfuric acid, and SO₃; to form a reaction mixture that is characterized by (i) a concentration of nitric acid therein that is in the range of about 2.0 to about 2.3 moles per mole of 1,3-dihalobenzene; (ii) a concentration of SO₃ therein that is in the range of about 1 to about 3 moles per mole of 1,3-dihalobenzene; (iii) a concentration of 1,3-dihalobenzene therein that is in the range of about 12 to about 24 weight percent; and (iv) a temperature of up to about 120° C.; and (b) stirring the reaction mixture at a temperature in the range of about −10° C. to about 70° C. to form a 1,3-dihalo-4,6-dinitrobenzene product. A 1,3-dihalo-4,6-dinitrobenzene product may be isolated from the reaction mixture at a temperature between about 0° C. and about 40° C.

In a preferred embodiment, any of the above steps of a process hereof may be run in the exclusion or substantial exclusion of oxygen, which may be accomplished by running under a blanket of nitrogen.

EXAMPLES

The advantageous attributes and effects of the processes hereof may be seen in a series of examples as described below. The embodiments of these processes on which the examples are based are representative only, and the selection of those embodiments to illustrate the invention does not indicate that materials, reactants, conditions, steps, techniques, or protocols not described in these examples are not suitable for practicing these processes, or that subject matter not described in these examples is excluded from the scope of the appended claims and equivalents thereof.

In the examples, the meaning of certain abbreviations is as follows: "DADNB" means 1,3-diamino-4,6-dinitrobenzene, "DCDNB" means 1,3-dichloro-4,6-dinitrobenzene, "g" means gram(s), "GC" means gas chromatography, "h" means hour(s), "L" means liter(s), "mL" means milliliter(s), and "wt %" means weight percent(age).

As used herein, the term "net yield" of a product denotes the actual, in-hand yield, i.e. the theoretical maximum yield minus losses incurred in the course of activities such as isolating, handling, drying, and the like. As used herein, the term "purity" denotes what percentage of an in-hand, isolated sample is actually the specified substance.

Example 1

Preparation in Glycol Plus Water

A three-necked 1 L flask was equipped with a thermocouple, magnetic stirrer and gas inlet tube connected to a flow meter and reflux condenser with gas outlet. The gas outlet was equipped with a three-way-splitter connecting the outlet to an oil bubbler and an N₂ line. The inlet tube was connected to an oil bubbler, a wash bottle and a three-way-splitter connected to N₂ and an NH₃ bottle. DCDNB (80.0 g, >99% pure) was suspended in 450 mL glycol (>99.8% pure, water <0.003%, obtained from Sigma-Aldich, Milwaukee, Wis., USA) and 10 mL deionized water. Nitrogen was purged through the inlet tube for 2 h under stirring before the mixture was heated to 140° C. The gas purge was switched to NH₃ and the flow rate was adjusted such that the amount released through the gas outlet was kept at minimum, and the flow rate and stirring were kept constant throughout the reaction. Conversion to product was controlled by GC analysis.

After 7 h, the conversion was complete and ammonia flow was turned off. The reaction suspension was allowed to cool to 60° C. before it was filtered. The yellow colored fine crystalline product was washed with two portions of about 50 mL of 60° C. ethylene glycol followed by 2×50 mL water followed by 2×50 mL methanol and dried under vacuum. The net yield was about 61 g (93%) and the purity was >99%. No glycol ether as represented by the structure of Formula (II)

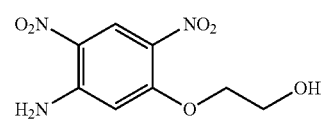

was observed.

Control A: Preparation in Dry Glycol

This run was conducted exactly as described in Example 1, using the same flow rates and stirring rates; however, no water was added to the reaction. After 7 h, no further conversion was observed. The reaction suspension was allowed to cool to 60° C. before it was filtered and the dark brown colored product was washed with two portions of about 50 mL of 60° C. ethylene glycol followed by 2×50 mL water followed by 2×50 mL methanol and dried under vacuum. The net yield was about 62 g (94%) and the purity was 96%. About 4 wt % of the glycol ether represented by the structure of Formula (II) was observed as by-product.

Example 2

Preparation in Glycol with Aqueous NH₃ Solution

A three-necked 0.5 L flask was equipped with a thermocouple, magnetic stirrer and precision addition funnel and reflux condenser with gas outlet. The gas outlet was equipped with a three-way-splitter connecting the outlet to an oil bubbler and an N₂ line. DCDNB (40.0 g, >99% pure) was suspended in 225 mL glycol (>99.8% pure, water <0.003%, obtained from Sigma-Aldrich, Milwaukee, Wis., USA), and the suspension was purged with N₂ for 2 h before the purge was removed and the mixture was heated to 140° C. under nitrogen. An aqueous ammonium hydroxide solution (56 g, 28 wt %) was added such that the amount released through the gas outlet was kept at minimum, and stirring was kept constant throughout the reaction. Addition was complete after 5 h, and the conversion was complete. The reaction suspension was allowed to cool to 60° C. before it was filtered. The yellow colored fine crystalline product was washed with two portions of about 50 mL of 60° C. ethylene glycol followed by 2×50 mL water followed by 2×50 mL methanol and dried under vacuum. The net yield was about 32 g (95%) and the purity was >99%. The presence of the glycol ether as represented by the structure of Formula (II) was not observed.

Where a range of numerical values is recited or established herein, the range includes the endpoints thereof and all the individual integers and fractions within the range, and also includes each of the narrower ranges therein formed by all the various possible combinations of those endpoints and internal integers and fractions to form subgroups of the larger group of values within the stated range to the same extent as if each of those narrower ranges was explicitly recited. Where a range of numerical values is stated herein as being greater than a stated value, the range is nevertheless finite and is bounded on its upper end by a value that is operable within the context of the invention as described herein. Where a range of numerical values is stated herein as being less than a stated value, the range is nevertheless bounded on its lower end by a non-zero value.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the subject matter hereof, however, may be stated or described as consisting essentially of certain features or elements, in which embodiment features or elements that would materially alter the principle of operation or the distinguishing characteristics of the embodiment are not present therein. A further alternative embodiment of the subject matter hereof may be stated or described as consisting of certain features or elements, in which embodiment, or in insubstantial variations thereof, only the features or elements specifically stated or described are present.

In this specification, unless explicitly stated otherwise or indicated to the contrary by the context of usage, amounts, sizes, ranges, formulations, parameters, and other quantities and characteristics recited herein, particularly when modified by the term "about", may but need not be exact, and may also be approximate and/or larger or smaller (as desired) than stated, reflecting tolerances, conversion factors, rounding off, measurement error and the like, as well as the inclusion within a stated value of those values outside it that have, within the context of this invention, functional and/or operable equivalence to the stated value.

What is claimed is:

1. A process for preparing 1,3-diamino-4,6-dinitrobenzene, which is represented by the structure of the following Formula (I):

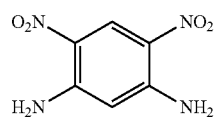

I comprising
(a) providing a reaction mixture that comprises 1,3-dihalo-4,6-dinitrobenzene, which is represented by the structure of the following Formula (III):

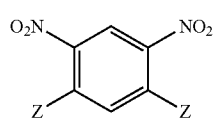

III wherein each Z is independently Cl or Br, in a solvent in the presence of ammonia and about 2 to about 25 wt % water (based on the combined weight of water and solvent in the reaction mixture), wherein the solvent comprises an aliphatic dihydric alcohol; and (b) heating the reaction mixture to convert the 1,3-dihalo-4,6-dinitrobenzene to 1,3-diamino-4,6-dinitrobenzene.

2. A process according to claim 1 wherein one or both Zs are Cl.

3. A process according to claim 1 wherein the reaction mixture is a suspension of 1,3-dihalo-4,6-dinitrobenzene in a mixture of solvent and water in contact with gaseous $NH_3$, wherein the suspension comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

4. A process according to claim 3 wherein the suspension is heated to a temperature in the range of about 100° C. to about 160° C.

5. A process according to claim 1 wherein the reaction mixture is provided by forming a suspension of 1,3-dihalo-4,6-dinitrobenzene in solvent, heating the suspension, and contacting the heated suspension with an aqueous ammonia solution to form a reaction mixture that comprises about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

6. A process according to claim 5 wherein the suspension is heated to a temperature in the range of about 100° C. to about 160° C.

7. A process according to claim 5 wherein the reaction mixture is heated to a temperature in the range of about 100° C. to about 160° C.

8. A process according to claim 1 wherein the reaction mixture is provided by contacting 1,3-dihalo-4,6-dinitrobenzene with a feed that comprises a solvent, $NH_3$ and water to form a reaction mixture that comprises a suspension of about 10 to about 25 wt % 1,3-dihalo-4,6-dinitrobenzene (based on the total weight of the whole reaction mixture) and about 2 to about 25 wt % water (based on the combined weight of water and solvent in the reaction mixture).

9. A process according to claim 8 wherein the reaction mixture is heated to a temperature in the range of about 100° C. to about 160° C.

10. A process according to claim 1 wherein the 1,3-diamino-4,6-dinitrobenzene product is filtered and washed with solvent and then water.

11. A process according to claim 10 wherein the filtrate containing solvent is collected and distilled, and the solvent is recovered and recycled to the reaction mixture.

12. A process according to claim 1 wherein a wet cake of 1,3-diamino-4,6-dinitrobenzene is recovered and dried.

13. A process according to claim 1 wherein 1,3-diamino-4,6-dinitrobenzene is slurried with water as a suspension and transferred to another reactor for further processing.

14. A process according to claim 1 further comprising: admixing a 1,3-dihalobenzene, which is represented by the structure of the following Formula (IX):

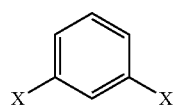

IX wherein each X is independently Cl or Br, with fuming nitric acid, sulfuric acid, and $SO_3$ to form a reaction mixture that is characterized by (1) a concentration of nitric acid therein that is in the range of about 2.0 to about 2.3 moles per mole of 1,3-dihalobenzene; (2) a concentration of $SO_3$ therein that is in the range of about 1 to about 3 moles per mole of 1,3-dihalobenzene; (3) a concentration of 1,3-dihalobenzene therein that is in the range of about 12 to about 24 weight percent; and (4) a temperature of up to about 120° C.; and stirring the reaction mixture at a temperature in the range of about −10° C. to about 70° C. to form a 1,3-dihalo-4,6-dinitrobenzene product; to provide a 1,3-dihalo-4,6-dinitrobenzene for incorporation into the reaction mixture of step (a).

15. A process according to claim 1 wherein the solvent comprises ethylene glycol.

\* \* \* \* \*